United States Patent [19]

Dubek et al.

[11] Patent Number: 5,914,135
[45] Date of Patent: Jun. 22, 1999

[54] LIQUID ANTACID COMPOSITIONS

[75] Inventors: John J. Dubek, Philadelphia; Gerard P. McNally, Strafford; Bruce P. Smith, Blue Bell, all of Pa.

[73] Assignee: McNeil-PPC, Inc., Skillman, N.J.

[21] Appl. No.: 08/838,239

[22] Filed: Apr. 16, 1997

[51] Int. Cl.$^6$ .......................... A61K 33/06; A61K 33/08; A61K 33/10; A61K 33/12

[52] U.S. Cl. .......................... 424/687; 424/601; 424/682; 424/683; 424/685; 424/686; 424/688; 424/689; 424/690; 424/691; 424/692; 424/693; 424/696; 424/697; 424/715; 424/716; 424/717; 424/684; 514/561; 514/819; 514/925; 514/926; 514/927; 514/820

[58] Field of Search ...................... 424/687, 692, 424/601, 682–686, 688–691, 693, 696–697, 715–717; 514/819, 561, 820, 925–927

[56] References Cited

U.S. PATENT DOCUMENTS

| | | | |
|---|---|---|---|
| 5,455,050 | 10/1995 | Beyerle et al. | 424/682 |
| 5,496,567 | 3/1996 | McLean | 424/692 |
| 5,498,426 | 3/1996 | Wilson et al. | 424/602 |

FOREIGN PATENT DOCUMENTS

| | | |
|---|---|---|
| 2179682 | 2/1997 | Canada . |
| WO 95/10290 | 10/1994 | WIPO . |

OTHER PUBLICATIONS

Preservative–Free AMD Self–Preserving Cosmetics And Drugs Principles And Practice; Edited by John J. Kabara and Donald S. Orth, pp. 244–247, 1996.

Microbiological Stability Of Oral Dosage Forms Problems With Liquid Antacids; S.T.P. Pharma 1 (8) 720–726, 1985; P. C. Schmidt, University of Marburg.

Chemical Abstract, Answer 1–18 IPA, Copyright 1997 ASHP.

Drug Development And Industrial Pharmacy, 13(8), 1429–1446 (1987).

Chemical Abstract, Answer 1–24 HCAPLUS Copyright 1997 ACS; 1996: 262743.

*Primary Examiner*—John Pak
*Attorney, Agent, or Firm*—Kenneth J. Dow

[57] ABSTRACT

Calcium carbonate liquid antacid compositions containing one or more pH adjusting agents to maintain the pH above 9.0, preferably above 9.5. The resultant antacid liquid possesses superior resistance to microbial attack and enhanced taste properties.

10 Claims, No Drawings

LIQUID ANTACID COMPOSITIONS

BACKGROUND OF THE INVENTION

1. Field of the Invention

The present invention relates to liquid antacid compositions and methods for their preparation. More particularly, the present invention relates to preservative-free calcium carbonate liquid antacid compositions containing an additional alkaline compound as a pH adjusting agent. The compositions have a final product pH of greater than 9.0 providing for an enhanced resistance to microbial contamination and a better tasting product.

2. Description of the Related Art

Gastric antacids are agents that neutralize or remove acid from the gastric contents. Antacids are widely used in the treatment of various gastrointestinal disorders such as peptic ulcers and gastritis. Antacids are also used for the relief of acid indigestion, heartburn, dyspepsia, sour stomach, reflux esophagitis and the like. The clinical use of antacids is based on their ability to neutralize stomach acid and increase the pH of gastric secretions. Although antacids do not neutralize all gastric acid, increasing gastric pH from 1.3 to 2.3 neutralizes 90% and increasing pH to 3.3 neutralizes 99% of gastric acid. For optimal healing of peptic ulcers, most clinicians believe that gastric pH should be maintained at about 3–3.5. Accordingly, it is desirable that an antacid feature a high acid neutralization capacity and a rapid rate of gastric acid neutralization.

Antacids used today are made from a variety of inorganic salts such as calcium carbonate, sodium bicarbonate, magnesium salts and aluminum salts. Magnesium hydroxide and aluminum hydroxide are the most potent magnesium and aluminum compounds and are often used in combination. In addition, magnesium oxide, magnesium carbonate, aluminum phosphate, magaldrate and magnesium trisilicate are also employed.

Antacids are available in both liquid suspensions as well as solid dosage forms. In general, liquid antacid suspensions are preferred to tablets or powders since they are more rapidly and effectively solubilized and have a greater ability to react with and neutralize gastric acid.

One of the major concerns with antacid liquids is the lack of patient compliance due to the poor taste properties of liquid preparations. In addition to the inherent taste of the antacid actives there is the bitter taste associated with the necessary preservatives that must be added. Liquid antacid preparations are generally susceptible to microbial contamination; Ref. "Microbiological Stability of Oral Dosage Forms, Problems with Liquid Antacids", S.T.P. Pharma 1 (8) 720–726 (1985). The pH of any aqueous based solution is critical to controlling the microbial growth within the solution. Generally, acidic solutions (less than pH 4.5) or alkaline solutions (above pH 9.5) are less susceptible to microbial growth than neutral solutions (pH 6–9); Ref. "Preservative-Free and Self-Preserving Cosmetics and Drugs", Ed. J. J. Kabara and D. S. Orth, pg.245–246 (1996). Under most circumstances, the ability to restrict this microbial growth can be aided by the addition of a preservative. The degradation of the preservative in solution can in turn be affected by the pH of the finished product. In most situations, there is a perfect match between the finished product's pH and the pH range at which the preservative is most efficacious.

Calcium carbonate in suspension typically has a pH value in the slightly alkaline range of 8.5–9.0; Ref. Ullmann's Encyclopedia of Industrial Chemistry, 5th Edition, Vol. A15, pg. 320. No preservative systems approved in the United States function optimally at this pH. The alkyl esters of parahydroxybenzoic acid (the parabens, e.g. butylparaben, methylparaben and propylparaben) are most widely used as preservatives because they offer the most efficacious option, but they degrade over time and this degradation process increases exponentially with an increase in pH; Ref. "A Comparative Study of the Effectiveness of Preservatives in Twelve Antacid Suspensions" Drug Development and Industrial Pharmacy 13(8), 1429–1446 (1987). Consequently, in order to achieve adequate preservative levels throughout the shelf life of a product with an alkaline pH, higher levels of the preservative must be added initially. This can affect the taste of the finished product however, because preservatives such as the parabens are known to have a poor taste.

Accordingly, there is a need for a preservative system for liquid antacid preparations having pH levels above 7 which effectively inhibits microbial contamination over the shelf life of the product without adversely affecting the taste of the finished product.

One way to inhibit degradation of the preservative would be to lower the pH of the antacid suspension. This may be done through the addition of buffers such as citric acid and tartaric acid. For example, U.S. Pat. No. 5,455,050 discloses calcium carbonate/magnesium salt antacid suspensions containing a carboxylic acid buffering agent such as tartaric acid. However, in order to lower the pH sufficiently to a level of around pH 7 where preservative degradation is minimal, large amounts of these buffers are required. The addition of such amounts of these acidic buffers can in turn adversely affect the acid neutralizing capacity of the antacid. U.S. Pat. No. 5,498,426 pertains to stabilizing the pH of a calcium carbonate suspension in the pH range of 7.5–8.5. It should be noted that these preparations still contain parabens which result in a poor tasting product and sub-optimal patient compliance. Thus, there is a need for a method of preserving calcium carbonate antacid liquid suspensions that would also result in a pleasant tasting product.

SUMMARY OF THE INVENTION

The invention relates to preservative-free calcium carbonate liquid antacid preparations having enhanced taste properties comprising calcium carbonate in admixture with one or more pH adjusting agents to maintain the pH above 9.0, preferably above 9.5. Superior resistance to microbial contamination is achieved due to the elevated pH. Also, a preservative is not required resulting in improved product taste properties. Further, the addition of a pH adjusting agent in accordance with the present invention advantageously provides a product which is pH stable; i.e. one which is capable of maintaining the pH above 9.0 over an extended period.

DETAILED DESCRIPTION

The invention relates in particular to calcium carbonate based liquid antacid preparations comprising an effective amount of a calcium carbonate antacid and optionally one or more additional acid neutralizing compounds, a pH adjusting agent to maintain the pH of the liquid preparation above 9.5 and optionally, one or more other pharmaceutically acceptable excipients. Preferably, the preparation contains 100 mg–2000 mg/5 ml calcium carbonate, and about 1 mg–500 mg/5 ml of pH adjusting agent.

The pH adjusting agents that are applicable for use in the present invention are those which are highly alkaline in aqueous solution having a pH greater than about 10.0. The amount of pH adjusting agent to raise and maintain the pH of the calcium carbonate preparation above 9.5 is in general an amount greater than 1 mg/5 ml. In addition, the pH adjusting agent added may also function as an additional active acid neutralizing compound, and accordingly, additional amounts of pH adjusting agent may be added if necessary for this purpose. The pH adjusting agent may be selected from any of the following compounds: magnesium hydroxide; magnesium oxide; magnesium phosphates; magnesium carbonate; magnesium hydroxide carbonate; magnesium glycinate; magnesium silicates; magnesium aluminum silicate; alkaline clays such as bentonite; zeolites; calcium oxide; calcium hydroxide; calcium phosphates; magaldrate; hydrotalcite; dihydroxyaluminum sodium carbonate; alkali metal hydroxides; phosphates; carbonates and bicarbonates; ammonium hydroxide; ammonium bicarbonate; ammonium carbonate; ethanolamine; diethanolamine; triethanolamine; tetrasodium ethylenediaminetetraacetic acid and its hydrates. One or more of such pH adjusting agents may be used to raise the pH of the calcium carbonate suspension above 9.5.

The amount of antacid in the preparation may conveniently be, for example, in the range of 2% to 40% w/v of the composition. A mixture containing from about 2 to about 25% w/v calcium carbonate and about 0.02 to about 10% pH adjusting agent may advantageously be employed. The calcium carbonate, and pH adjusting agents are generally utilized as individual powders, preferably micronized powders.

The pH adjusting agent material is added in an amount to bring the pH of the preparation to a level above 9.5. For example, the pH adjusting agent may constitute 0.02 to 10% w/v of the composition, generally in the range of 1–500 mg/5 ml. The pH of the final product is above 9.5 preferably in the range of 9–12.5.

The composition according to the invention, in unit dosage form, may be administered, for example 1 to 4 times per day. The dosage will depend on the active agents that are employed, the condition being treated and the age and weight of the patient. Typical dosages include about 5–30 mls of the preparation containing the dose of antacid selected to achieve the desired acid neutralizing effect. A suitable dose range for calcium carbonate is 100 mg to 2000 mg.

In addition to calcium carbonate, the liquid compositions of the invention may contain one or more additional acid neutralizing compounds commonly used in conventional antacid suspensions. For instance, the liquid suspension may contain, in admixture with the calcium carbonate, such additional acid neutralizing compounds as magnesium trisilicate, magnesium hydroxide and the like. As stated, the pH adjusting agent utilized may also act as additional acid neutralizing compound and any of the pH adjusting agents previously recited may be used for this purpose.

The liquid compositions of the invention are aqueous suspensions containing the active ingredients in admixture with pharmaceutically acceptable excipients typically found in aqueous suspensions for oral administration. Such excipients may be suitable suspending agents, for example, sodium alginate, polyvinylpyrrolidone, gum tragacanth, gum acacia, xanthan gum, locust bean gum and cellulose derivatives such as sodium carboxymethylcellulose, microcrystalline cellulose, hydroxy ethylcellulose, methyl cellulose or hydroxypropyl methylcellulose or mixtures thereof. Also included may be dispersing or wetting agents such as sorbitan esters or lecithin, antigelling additives, surface modifiers, aqueous or non-aqueous vehicles such as sorbitol solution, ethyl alcohol or fractionated vegetable oils, or diluents.

The compositions may also contain flavorings, colorants and/or sweeteners as appropriate. Suitable flavorants include fruit flavors, peppermint, licorice or bubble gum flavors. The sweetening agents may be for example bulk sweeteners or polyols (e.g. maltitol, sorbitol) and/or intense sweeteners such as saccharin, aspartame or acesulfame K.

Other active agents may be added to the preparation. For instance, antiflatulents, analgesics, antidiarrheals, $H_2$ receptor antagonists, proton pump inhibitors, antispasmodic agents or anti-foaming agents like simethicone may be added as well as other gastrointestinal agents in dosage amounts conventionally used in the treatment of gastrointestinal dysfunction.

The liquid antacid compositions of the present invention may be prepared according to conventional techniques well known in the pharmaceutical industry. Thus, for example, the antacid, and the pH adjusting agent may be admixed, if desired, with suitable excipients and dispersed in the aqueous vehicle.

As stated, the use of a pH adjusting agent to raise the pH of the antacid composition of the present invention provides for superior taste properties and resistance to microbial growth. The use of a pH adjusting agent to raise the pH allows one to do this without compromising the acid neutralizing capacity of the antacid. Additionally, since an added preservative such as parabens is not required the taste of the finished product is greatly improved over the prior art. Additionally, the expected shelf life of the product may be increased significantly over current commercially available calcium carbonate containing antacid suspensions since the product is essentially preservative-free and therefore is not subject to the limited shelf-life due to degradation of the preservatives.

As stated, the use of the pH adjusting agent in accordance with the present invention provides a product which is pH stable over the shelf life of the product. Quite unexpectedly, the addition of the pH adjusting agent in amounts as set forth herein are capable of buffering the composition and maintaining the pH at a level sufficient to provide resistance to microbial degradation over the shelf life of the product.

In order to further illustrate the present invention and the advantages thereof, the following specific examples are given, it being understood that these examples are intended only to be illustrations without serving as a limitation on the scope of the present invention.

EXAMPLE 1

Liquid Antacid Composition Containing the pH Adjusting Agent Magnesium Hydroxide A liquid antacid composition of the present invention was prepared containing the following ingredients:

| Ingredient | mg/5 ml | gm/100 ml |
| --- | --- | --- |
| Calcium Carbonate | 400 | 8.0 |
| Purified Water | 3935 | 78.7 |
| Sorbitol Solution | 1000.0 | 20 |
| Xanthan Gum | 13.0 | 0.26 |
| Hydroxyethylcellulose | 5.0 | 0.1 |
| pH adjusting agent, $Mg(OH)_2$ | 120.0 | 2.4 |

-continued

| Ingredient | mg/5 ml | gm/100 ml |
|---|---|---|
| Flavor | 25.0 | 0.50 |
| Sodium Saccharin | 1.425 | 0.0285 |

In a suitable preparation vessel such as a clean stainless steel vessel, the sorbitol and water are added. The hydroxyethylcellulose and the xanthan gum are added and mixed for thirty minutes. The calcium carbonate is then added and mixed for fifteen minutes. The magnesium hydroxide, flavor and saccharin are then added and the mixture is stirred for 15 minutes. The suspension is then milled and pasteurized at 68° C. and filled into bottles.

EXAMPLE 2

Liquid Antacid Composition Containing the pH Adjusting Agent Sodium Carbonate

A liquid antacid composition of the present invention was prepared containing the following ingredients:

| Ingredient | mg/5 ml | gm/100 ml |
|---|---|---|
| Calcium Carbonate | 400 | 8.0 |
| Purified Water | 3935 | 78.7 |
| Sorbitol Solution | 1000.0 | 20 |
| Xanthan Gum | 13.0 | 0.26 |
| Hydroxyethylcellulose | 5.0 | 0.1 |
| pH adjusting agent, $Na_2(CO_3)$ | 10.0 | 0.2 |
| Flavor | 25.0 | 0.50 |
| Sodium Saccharin | 1.425 | 0.0285 |

In a suitable preparation vessel such as a clean stainless steel vessel, the sorbitol and water are added. The hydroxyethylcellulose and the xanthan gum are added and mixed for thirty minutes. The calcium carbonate is then added and mixed for fifteen minutes. The sodium carbonate, flavor and saccharin are then added and the mixture is stirred for 15 minutes. The suspension is then milled and pasteurized at 68° C. and filled into bottles.

EXAMPLE 3

Liquid Antacid Composition Containing the pH Adjusting Agent Dihydroxyaluminum Sodium Carbonate (DASC)

| | mg/5 ml | g/1 L |
|---|---|---|
| pH Adjusting Agent (DASC) | 400.0 | 8.0 |
| $CaCO_3$ powder | 800.0 | 16.0 |
| Simethicone (30% Emulsion) | 100 | 2.0 |
| Sorbitol (70% soln.) | 1000.0 | 20.0 |
| Xanthan Gum | 16.250 | 3.25 |
| Purified Water | 3400.0 | 68.0 |
| Flavor | 25.00 | 5.0 |
| Sodium Saccharin | 1.425 | 0.285 |

Place 400 g of deionized water and 200 g of 70% sorbitol solution in a 1.5 liter vessel equipped with an IKA mixer. With the agitator set at high speed add 32.5 g of xanthan gum to the mixture and mix until all of the gum has hydrated. When the gum has been completely dispersed add the 20 g of 30% simethicone emulsion to the vessel also under high speed agitation. Once the simethicone emulsion has been completely dispersed add the 160 g of calcium carbonate 10 and the following ingredients in sequence; 80 g of DASC powder, 50 g of flavor, 2.85 g of sodium saccharin, finally add 280 g of water. The suspension was then homogenized and pasteurized into plastic bottles.

EXAMPLE 4

Liquid Antacid Composition Containing the pH Adjusting Agent Magnesium Hydroxide A liquid antacid composition of the present invention was prepared containing the following ingredients:

| Ingredient | mg/5 ml | gm/100 ml |
|---|---|---|
| Calcium Carbonate | 1500 | 8.0 |
| Purified Water | 3165 | 79.5 |
| Sorbitol Solution | 1000.0 | 20 |
| Xanthan Gum | 13.0 | 0.26 |
| Hydroxyethylcellulose | 5.0 | 0.1 |
| pH adjusting agent, $Mg(OH)_2$ | 30.0 | 6.0 |
| Flavor | 25.0 | 0.50 |
| Sodium Saccharin | 1.425 | 0.0285 |

In a suitable preparation vessel such as a clean stainless steel vessel, the sorbitol and water are added. The hydroxyethylcellulose and the xanthan gum are added and mixed for thirty minutes. The calcium carbonate is then added and mixed for fifteen minutes. The magnesium hydroxide, flavor and saccharin are then added and the mixture is stirred for 15 minutes. The suspension is then homogenized at 500 psi. and pasteurized at 68° C. and filled into bottles.

pH Buffering

The pH of the composition of Example 1, containing 120 mg/5 ml of magnesium hydroxide, was tested over time and compared with a control composition containing no pH adjusting agent. The results are set forth in Table 1.

TABLE 1

| Ex # | Init. | 1 Wks | 2 Wks | 4 Wks | 6 Wks |
|---|---|---|---|---|---|
| Cont. | 8.9 | 8.9 | 8.9 | 8.9 | 8.9 |
| Ex 1 | 9.9 | 9.9 | 9.9 | 9.9 | 9.9 |

Control (No pH adjusting agent)
Example 1 (Magnesium Hydroxide 120 mg/5 ml)

The foregoing table demonstrates that the pH adjusting agent was effective in maintaining the pH of the antacid composition above 9.5 over the period of time measured.

Antimicrobial Effectiveness Testing

The liquid antacid composition of Example 1 and a comparative formulation which did not contain the pH adjusting agent but did contain preservative were both tested for resistance to microbial growth in accordance with the procedures established by the US Pharmacopoeia, using the USP standard organisms. Both samples were also tested with USP organisms listed for inclusion in USP AME testing; Escherichia Coli ATCC 8739 and *Pseudomonas aeroginosa* ATCC 9027.

The acceptable criteria for this procedure is as follows; for viable bacteria, not more than 150% from the initial inoculation at 14 and 28 days and for viable yeast and molds, not more than 150% of the initial inoculation at 14 and 28 days. For the second inoculation, the same criteria is used. The results are set forth below in Tables 2 and 3

TABLE 2

SAMPLE 1
COMPARATIVE FORMULATION WITHOUT pH ADJUSTING AGENT

| | S. aureus ATCC 6538 | Ps. picketti ATCC 27511 | Ps. aerug ATCC 9027 | E. coli ATCC 8739 | C. albicans ATCC 10231 | A. niger ATCC 16404 |
|---|---|---|---|---|---|---|
| Original Challenge | | | | | | |
| Inoc Level | $23 \times 10^6$ | $18 \times 10^6$ | $61 \times 10^6$ | $73 \times 10^6$ | $29 \times 10^5$ | $58 \times 10^4$ |
| Initial | $64 \times 10^3$ | <10 | $20 \times 10^3$ | $55 \times 10^3$ | $8 \times 10^3$ | $2 \times 10^3$ |
| 1 Week | <10 | <10 | $20 \times 10^4$ | $14 \times 10^5$ | $30 \times 10^2$ | 10 |
| 2 Weeks | <10 | <10 | $51 \times 10^4$ | $13 \times 10^5$ | <10 | 20 |
| 3 Weeks | <10 | <10 | $62 \times 10^4$ | $14 \times 10^5$ | <10 | 10 |
| 4 Weeks | <10 | <10 | $73 \times 10^5$ | $37 \times 10^5$ | <10 | <10 |
| Reinoc Re-Challenge | | | | | | |
| Inoc Level | $11 \times 10^5$ | $13 \times 10^5$ | | | $57 \times 10^5$ | $17 \times 10^6$ |
| Initial | $56 \times 10^3$ | <10 | | | $18 \times 10^3$ | $6 \times 10^3$ |
| 1 Week | <10 | <10 | | | <10 | 20 |
| 2 Weeks | <10 | <10 | | | <10 | 10 |
| 3 Weeks | <10 | <10 | | | <10 | 30 |
| 4 Weeks | <10 | <10 | | | <10 | 30 |

TABLE 3

SAMPLE 2
FORMULATION OF EXAMPLE 1

| | S. aureus ATCC 6538 | Ps. picketti ATCC 27511 | Ps. aerug ATCC 9027 | E. coli ATCC 8739 | C. albicans ATCC 10231 | A. niger ATCC 16404 |
|---|---|---|---|---|---|---|
| Original Challenge | | | | | | |
| Inoc Level | $91 \times 10^6$ | $71 \times 10^6$ | $94 \times 10^6$ | $88 \times 10^6$ | $55 \times 10^6$ | $13 \times 10^6$ |
| Initial | $82 \times 10^3$ | 240 | $78 \times 10^3$ | $69 \times 10^3$ | $47 \times 10^3$ | $66 \times 10^3$ |
| 1 Week | 80 | 210 | 80 | <10 | <10 | $40 \times 10^2$ |
| 2 Weeks | <10 | <10 | <10 | <10 | <10 | $28 \times 10^2$ |
| 3 Weeks | <10 | <10 | <10 | <10 | <10 | $20 \times 10^2$ |
| 4 Weeks | <10 | <10 | <10 | <10 | <10 | $20 \times 10^2$ |
| Reinoc Re-Challenge | | | | | | |
| Inoc Level | $42 \times 10^6$ | $11 \times 10^7$ | $11 \times 10^7$ | $67 \times 10^6$ | $16 \times 10^7$ | $13 \times 10^6$ |
| Initial | $18 \times 10^4$ | $94 \times 10^3$ | $26 \times 10^3$ | $31 \times 10^3$ | $43 \times 10^3$ | $27 \times 10^3$ |
| 1 Week | <10 | <10 | <10 | <10 | <10 | $30 \times 10^3$ |

The foregoing results indicate that, for the organisms *Escherichia coli* ATCC 8739 and *Pseudomonas aeruginosa* ATCC 9027, the comparative formuation without pH adjusting agent did not pass the above acceptance criteria but the liquid $CaCO_3/Mg(OH)_2$ sample of Example 1 did pass the test. Thus, only the liquid $CaCO_3/Mg(OH)_2$ sample of the present invention having pH adjusting agent met the criteria for resistance to microbial growth using the USP organisms: *E. coli* and *Ps. aeruginosa*.

We claim:

1. A preservative-free liquid antacid preparation being pH stable during its shelf life consisting essentially of:
    a) from about 2% to about 40% w/v calcium carbonate;
    b) an amount of magnesium hydroxide pH adjusting agent capable of maintaining the antacid preparation at a pH of greater than about 9.0; and
    c) optionally, one or more other pharmaceutically acceptable excipients; in an aqueous vehicle wherein the pH of the liquid antacid preparation is greater than about 9.0.

2. A liquid antacid preparation according to claim 1, consisting essentially of 100 mg–2000 mg/5 ml calcium carbonate and 1 mg–500 mg/5 ml magnesium hydroxide pH adjusting agent in association with one or more pharmaceutically acceptable excipients.

3. A liquid antacid preparation according to claim 1, wherein the pH of the final product is above 9.5.

4. A liquid antacid preparation according to claim 1, wherein the pH of the final product is in the range of greater than about 9.0 to 12.5.

5. A liquid antacid preparation according to claim 2, wherein the amount of magnesium hydroxide is 120 mg/5 ml.

6. A method for neutralizing excess stomach acid in a human or lower animal which comprises orally administering to said human or lower animal an effective amount of a liquid antacid composition of claim 1.

7. A method for the treatment of a gastrointestinal disorder in a human which comprises administering to said human an effective amount of a liquid antacid composition of claim 1.

8. A method according to claim 7 wherein the gastrointestinal disorder is selected from the group consisting of acid indigestion, heartburn, dyspepsia, sour stomach, and reflux esophagitis.

9. A preservative-free liquid antacid preparation being pH stable during its shelf life consisting essentially of:
    a) from about 2% to about 40% w/v calcium carbonate;
    b) one or more additional acid neutralizing compounds;
    c) an amount of magnesium hydroxide pH adjusting agent capable of maintaining the antacid preparation at a pH of greater than about 9.0; and
    d) optionally, one or more pharmaceutically acceptable excipients; in an aqueous vehicle wherein the pH of the liquid antacid preparation is then about 9.0.

10. A preservative-free liquid antacid preparation being pH stable during its shelf life consisting essentially of:
    a) from about 2% to about 40% w/v calcium carbonate;
    b) one or more active agents used in the treatment of gastrointestinal dysfunction;
    c) an amount of magnesium hydroxide pH adjusting agent capable of maintaining the antacid preparation at a pH of greater than about 9.0; and
    d) optionally, one or more pharmaceutically acceptable excipients; in an aqueous vehicle wherein the pH of the liquid antacid preparation is greater than about 9.0.

* * * * *